(12) United States Patent
Sutan

(10) Patent No.: US 9,891,198 B2
(45) Date of Patent: Feb. 13, 2018

(54) METHOD OF ANALYSING GAS CHROMATOGRAPHY DATA

(71) Applicant: I-VIGILANT TECHNOLOGIES LIMITED, Aberdeen (GB)

(72) Inventor: Anwar Sutan, Aberdeen (GB)

(73) Assignee: I-VIGILANT TECHNOLOGIES LIMITED, Aberdeen (GB)

( * ) Notice: Subject to any disclaimer, the term of this patent is extended or adjusted under 35 U.S.C. 154(b) by 857 days.

(21) Appl. No.: 13/854,264

(22) Filed: Apr. 1, 2013

(65) Prior Publication Data
US 2013/0304393 A1    Nov. 14, 2013

(30) Foreign Application Priority Data

Apr. 2, 2012 (GB) .................................. 1205915.0
Oct. 23, 2012 (GB) .................................. 1219051.8

(51) Int. Cl.
*G01N 30/86* (2006.01)
*G01N 30/20* (2006.01)

(52) U.S. Cl.
CPC ..... *G01N 30/8665* (2013.01); *G01N 30/8675* (2013.01); *G01N 2030/201* (2013.01); *G01N 2030/202* (2013.01); *G01N 2030/207* (2013.01)

(58) Field of Classification Search
CPC ........... G01N 30/8665; G01N 30/8675; G01N 2030/626; G01N 35/006936; G01N 2201/127; G01N 2201/1288
USPC .................................................. 702/85, 100
See application file for complete search history.

(56) References Cited

U.S. PATENT DOCUMENTS

2012/0016597 A1* 1/2012 Sutan ................. G01N 30/8665
                                                                                702/24
2012/0078533 A1  3/2012 Nouvelle

FOREIGN PATENT DOCUMENTS

GB        1584978       5/1981
JP      2004-020323     1/2004

OTHER PUBLICATIONS

Estimating uncertainty in analytical procedures based on chromatographic techniques Review Article, pp. 882-891, Piotr Konieczka, Jacek Namieśnik, Journal of Chromatography A vol. 1217, Issue 6, pp. 791-924 (Feb. 5, 2010).*

(Continued)

*Primary Examiner* — Manual Rivera Vargas
(74) *Attorney, Agent, or Firm* — Nixon & Vanderhye P.C.

(57) ABSTRACT

A method of analyzing gas chromatography data is described. The method, a first response factor data set acquired from a gas chromatograph (GC) apparatus during a procedure on a calibration or reference gas sample at a first time is received. One or more additional response factor data sets acquired from the gas chromatograph apparatus during a procedure on a calibration or reference gas sample from one or more later times are received. The method comprises calculating a measure of uncertainty for at least one compound of the reference gas sample from the first and additional response factor data sets. The one or more later times are during an operational period of the gas chromatograph apparatus. The measure of uncertainty may be used to, for example, identify the necessity to perform a maintenance action in the GC or to assess whether the GC is in a healthy or unhealthy condition.

19 Claims, 4 Drawing Sheets

(56) References Cited

OTHER PUBLICATIONS

Kowalsky et al., Correlation of the Response Factors of Thermal-Conductivity Detector With Molecular Weight for Methylsiloxanes; Journal of Chromatography A, vol. 130, 1977; pp. 351-353.

Sutan et al., Three Columns Gas Chromatograph Analysis Using Correlation Between Component's Molecular Weight and Its Response Factor; 27th International North Sea Flow Measurement Workshop; Oct. 20-23, 2009; Tonsberg, Norway; pp. 1-15.

Standard Test Method for Analysis of Natural Gas by Gas Chromatography; American Society for Testing and Material; Originally Adopted in 1996; pp. 1-16.

Standard Practice for On-line/At-line Heating Value Determination of Gaseous Fuels by Gas Chromatography; Originally Adopted in 2005; pp. 1-4.

Analysis for Natural Gas and Similar Gaseous Mixtures by Gas Chromatography; Gas Processors Association; Originally Adopted in 1961; pp. 1-17.

Natural Gas—Determination of Composition With Defined Uncertainty by Gas Chromatography—Part 5: Determination of Nitrogen, Carbon Dioxide and C1 to C5 and C6+ Hydrocarbons for a Laboratory and On-line Process Application Using Three Columns; ISO, First Edition; Apr. 1, 2000; pp. 1-14.

Danalyzer/2350A Gas Chromatograph—Hardware Reference Manual; Section 1.6 Theory of Operation; pp. 1-11 and 1-18 and Addendum 1, Drawing BE-17204 Entitled: Flow Configuration Backflush to Measure Dual Column With SSO; Emerson Process Management; Dec. 2002.

\* cited by examiner

METHOD OF ANALYSING GAS CHROMATOGRAPHY DATA

This application claims priority to GB Patent Application No. 1205915.0 filed 2 Apr. 2012 and GB Patent Application No. 1219051.8 filed 23 Oct. 2012, the entire contents of each of which are hereby incorporated by reference.

The present invention relates to the field of gas chromatography, and in particular to a method of analysing gas chromatography data, and methods of calibrating, monitoring and/or maintaining gas chromatography equipment. Embodiments of the invention are applicable to on-site or online gas chromatography measurements of natural gas composition.

BACKGROUND TO THE INVENTION

Gas chromatography techniques are used in analytic chemistry applications to separate and/or analyse components of a mixture. Gas chromatography uses a carrier gas as its mobile phase and a layer of liquid or polymer on a solid support as its stationary phase, located in a metal tube referred to as a column. Gaseous compounds in a sample being analysed interact with the stationary phase as it passes through the column with the carrier gas. Different compounds interact at different rates and elute at different times. Analysis of the response factors of the compounds allows information to be derived about the compounds.

Gas chromatography has numerous industrial applications. For example, it is used in the oil and gas industry to analyse the composition of a natural gas, which typically includes inert components and hydrocarbon components ranging from $C_1$ to $C_{7+}$: i.e. Nitrogen, $CO_2$, methane, ethane, propane, isobutane, n-butane, isopentane, n-pentane, hexanes, heptanes and higher alkanes. In order to analyse such a sample in a practical time frame and without temperature ramping, a multi column separation technique is required. A $C_{6+}$ gas chromatograph (GC) system is configured to analyse components from $C_1$ to $C_5$ separately, with $C_6$ and higher compounds giving a single output. A $C_{7+}$ GC system is configured to analyse components from $C_1$ to $C_6$ separately, with $C_7$ and higher compounds giving a single output.

A typical three column GC design is shown in FIG. 1 generally at 100, and uses chromatograph valves 101, 102, three columns 103, 104, 105, a restrictor 106, a reference detector 108 and measuring detector 107 in a controlled temperature chamber 109. The detectors 107, 108 are thermistors, where resistance changes are dependent on the temperature. The reference and measuring detectors form a balanced Wheatstone bridge. Helium is the preferred carrier gas because it has high thermal conductivity, although Nitrogen, Hydrogen and Argon can also be used in special circumstances. FIG. 1 shows a flow path of the $C_1$, $C_2$, and $C_6$ compounds through the third column 105.

With only carrier gas flowing across the two detectors 107, 108, the Wheatstone bridge is in balance. In the measuring detector, the sample gases passing across the thermistor cause thermal conductivity changes, which result in a change of thermistor heat exchange rate. This in turn results in a change of the temperature of the thermistor. The change of temperature results in a change of resistance in the measuring detector and unbalances the Wheatstone bridge. The magnitude of the voltage created by the unbalanced bridge and the time taken to pass through the detector then forms a response curve; the area under the curve is proportional to the amount of the component in the carrier gas stream.

Actuation of the valves controls the flow of gases in the GC. There are three important valve timings on the three-column chromatograph as follows:

1. Valve 101 is actuated to allow the heaviest component ($C_{6+}$ in a $C_{6+}$ GC application, or $C_{7+}$ in a $C_{7+}$ GC application) to be back-flushed. The back-flush is initiated after $C_5$ and lighter components (in a $C_{6+}$ GC system) or after $C_6$ and lighter components (in a $C_{7+}$ GC) are eluted from column 103 to column 104, but before the heaviest component (i.e. $C_{6+}$ or $C_{7+}$) leaves column 103.
2. Valve 102 is actuated to trap the light components in column 105. The valve actuation has to be after all of the $C_2$ (ethane) is eluted into column 105 but before any $C_3$ (propane) leaves column 104.
3. Valve 102 is actuated to allow light components to leave column 105. The valve actuation has to be after all of the middle components ($C_3$ to $C_5$ in a $C_{6+}$ application; $C_3$ to $C_6$ in $C_{7+}$ application) clear the measurement detector.

During calibration, a calibration gas of known composition is analysed. The gas chromatographs (GCs) analyse the sample and the components of the composition generate peaks in the output of the detectors. The area measured under the peak is divided by the known gas molar percentage of that component to derive a response factor for that component. That is, the response factor RF is calculated as follows:

$$RF = \text{Peak Area/Gas mole \%} \quad \text{(Eq.1)}$$

During normal analysis of an unknown sample, the response factor RF is used to calculate the unknown gas mole percentage of each component from the measured peak area and the response factor, according to:

$$\text{Gas mole \%} = \text{Peak Area/RF} \quad \text{(Eq.2)}$$

Gas chromatographs (GCs) may be delivered from a factory with a multilevel calibration already programmed. The multilevel calibration is performed on a number of separate gas samples corresponding to the compounds that the gas chromatograph is configured to detect. The multilevel calibration establishes the ability of the GC detector to measure a specific component and a response factor curve which is measured over a specified range of each component's concentration. The multilevel calibration also establishes the repeatability of measurements of each component over a specified concentration range. While this is an effective method to handle the linearity of the detector, many sets of gases at varying concentrations are required to obtain the multilevel calibration parameters. It is common for component parts of the GC, such as columns, diaphragms, detectors, etc. to be changed on site, after which the GC may require a new set of multilevel calibration parameters. For a number of reasons it is not always practical to perform multilevel calibration on site or in the field, not least because of the time consuming nature of a multilevel calibration process.

Other calibration techniques are used in the field. For example, a periodic auto-calibration may be performed using a certified gas sample mixture to ensure that the GC is functioning within a defined specification. The frequency at which the calibrations are performed is determined by the stability of the GC calibration and may for example be daily, weekly or monthly. However, if the GC does not provide a linear response or if it becomes necessary to use a certified gas with a different composition, errors may be introduced.

On-line (in the field or on-site) gas chromatography is now commonplace in the North Sea and is frequently used within Fiscal and Custody Transfer measurement systems. The uncertainty of the analysis from the gas chromatograph (GC) is of the utmost importance with the resultant analysis frequently at the core of economic transactions [1].

In recent years there has been increased interest in condition based monitoring (CBM) and in-situ verification of measurement devices. For example, publications can be found on ultrasonic meters [2], leading last year to the DECC policy statement outlining generic minimum requirements that would allow CBM to be considered. Similar assertions are being made regarding on-line verification of on Coriolis Meters [3]. Orifice plates have also recently seen significant effort put in to the development of diagnostic capabilities [4] Error! Reference source not found.

However, surprisingly, it would be reasonable to state that although the correct functioning of the GC is critical in today's measurement systems, comparatively little attention has been paid to verification and monitoring strategies [5, 6, 7, 8]. Although the modern gas chromatograph is an extremely repeatable device there remain several fundamental issues. For example, if the valve timing in the GC is wrong or drifts over time a systematic error can ensue. A recent study performed by the applicant identified a situation where such an error was present, and if it remained undetected, would have resulted in an on-going error in the calorific value of natural gas of up to 1.4%. For a typical production volume of gas of 3 to 4 million $m^3$ per month and taking an example gas price of $90 per 1000 $m^3$ this error would equate to a value of around £270,000 to £360,000 per month. Under the assumption of suitable sampling and conditioning the uncertainty of the GC measurement is generally driven by the linearity and the repeatability of the GC and the quality of the (certified) reference gas mixture. Various methods presently exist which may be used to obtain the GC repeatability. ISO 10723 [9] describes a method of performance evaluation using multiple calibration gas compositions to obtain the linearity of the GC as well as its repeatability. ASTM D1945 [10] provides a standard test method for the analysis of gas with a GC with stated levels for the expected repeatability and reproducibility.

However, these methods are only valid as long as the GC maintains the performance characteristics measured on the day of the test. ISO 6974 [11] describes data processing for the tailored analysis of natural gas with the aim of defining the uncertainty in the mole fractions of the component measured. However there remains little practical guidance on how to implement Condition Based Monitoring of on-site gas chromatographs.

A common method used in industry utilises measurements obtained every few minutes over a predefined period (for example, every four minutes during a 48 hours period), to obtain an uncertainty value for the GC chromatograph. The composition of a natural gas reference sample is measured every four minutes during the 48 subsequent hours after a calibration with a different reference sample has been made. The measurements taken during the 48 hours period are used to calculate a value representing repeatability relative uncertainty of the GC and its measurements.

This method may be carried out when the GC is in the laboratory or at the factory and although it is not usual, it can also be carried out when a GC is on-site. The uncertainty value obtained in the factory or in the laboratory is used in conjunction with composition measurements taken when the GC is on-site long after the repeatability relative uncertainty value has been obtained. This repeatability relative uncertainty value might not be representative of the actual GC uncertainty after several days or weeks after the GC is installed on-site and therefore the economic transactions based on the measured natural gas compositions and the repeatability relative uncertainty value obtained in the laboratory or factory might be overestimated or underestimated.

It is amongst the aims and objects of the present invention to provide improved methods of analysing gas chromatography data, and in particular, improved methods of uncertainty monitoring for gas chromatography apparatus. Additional aims include providing methods of calibrating, monitoring and/or maintaining gas chromatography equipment. The invention presents a novel method for monitoring a GC whilst also providing an on-line estimate of the overall uncertainty in the natural gas composition measurements which overcomes or at least mitigates one or more drawbacks of the previously proposed monitoring and maintenance scheduling methods for on-site gas chromatographs.

Further aims and objects of the invention will become apparatus from the following description.

SUMMARY OF THE INVENTION

According to a first aspect of the invention, there is provided a method of analysing gas chromatography data comprising:

receiving a first response factor data set acquired from a gas chromatograph apparatus during a procedure on a calibration or reference gas sample at a first time;

receiving one or more additional response factor data sets acquired from the gas chromatograph apparatus during a procedure on a calibration or reference gas sample from one or more later times;

calculating a measure of uncertainty of at least one compound of the reference gas sample from the first and additional response factor data sets;

wherein the one or more later times are during an operational period of the gas chromatograph apparatus.

Preferably the calibration or reference gas sample is a working reference mixture.

The operational period is preferably a period in which the gas chromatograph (GC) apparatus is in normal use, e.g. performing tests on unknown gas samples, and may be a period in which the GC apparatus is used to perform composition analyses on natural gas samples (which may be collected from hydrocarbon production or exploration operations). The one or more additional response factor data sets preferably comprises a plurality of data sets, which may be acquired over the operational period. For example, the one or more additional response factor data sets may comprise data sets collected daily or at regularly intervals interspersed between performing tests on unknown gas samples.

The measure of uncertainty data may therefore be real-time or live uncertainty information pertaining to the current condition of the GC. Alternatively, the measure of uncertainty data may be updated at regular or irregular intervals during a period of operation. For example, calculating a measure of uncertainty data may be carried out after every calibration of the GC. Alternatively calculating a measure of uncertainty data may be carried out after a selected number of calibrations or after a selected operational period.

The method may use historical reference (or "footprint") data generated when the GC is known to be functioning correctly. The footprint data may comprise data such as oven temperature, carrier gas pressure, carrier gas flow rate, and/or response factor etc. This footprint data can be used to analyze historical calibration results.

Calculating a measure of uncertainty may comprise calculating normalised compositions derived from calculated peak areas and/or historical response factors. The calculated peak areas may be derived from historical calibration data which may be obtained from a written register of calibration data, or may be obtained from a data storage device which may or may not be connected to the GC.

The use of normalised compositions for calculating a measure of uncertainty reduces the sensitivity of the uncertainty to possible changes in the compositions of the calibration gas. This may be useful in the event that a calibration gas needs to be replaced or is consumed and a full bottle needs to be supplied.

Calculating a measure of uncertainty may comprise calculating a standard relative uncertainty. Equivalent or similar statistical parameters may be used for calculating a measure of the uncertainty as an alternative without departing from the principles of the invention.

Calculating a measure of uncertainty may comprise calculating a combined relative uncertainty value. The combined relative uncertainty value may be calculated by combining two or more of a relative uncertainty of the calibration gas, an uncertainty of at least one compound derived from the GC reproducibility and/or a repeatability relative uncertainty. The method may comprise calculating a combined relative uncertainty value for at least one compound, and preferably comprises calculating a combined relative uncertainty value for multiple compounds.

Calculating a measure of uncertainty may comprise calculating a relative sensitivity of a desired gas property to a change in concentration of at least one compound. The gas property may be selected form the group comprising: calorific value, density, thermal conductivity, compressibility, and molecular weight.

Calculating a measure of uncertainty may comprise calculating a combined standard uncertainty of a gas property, which may comprise combining a calculated relative sensitivity of a desired gas property with a standard relative uncertainty. Alternatively, or in addition, the calculating a combined standard uncertainty of a gas property may comprise combining a calculated relative sensitivity of the desired gas property with a combined relative uncertainty.

Additionally, calculating a measure of uncertainty may include calculating a combined expanded uncertainty of a gas property. This may be done by using a numerical coverage factor. A preferred coverage factor has a value of 2, but other values may be adopted.

The method may comprise comparing the measure of uncertainty with a predetermined threshold, and/or may comprise determining an operating condition of the gas chromatograph, for example whether it is operating in a healthy condition.

The method may comprise identifying or scheduling a requirement for one or more maintenance operations on the GC apparatus. The maintenance operation may be selected form the group comprising: a valve replacement, a column replacement, a calibration gas replacement, a troubleshooting method (e.g. for identifying what detailed action is needed); or a general maintenance service which addresses all common critical maintenance issues.

According to a second aspect of the invention, there is provided a method of analysing gas chromatography data comprising:

receiving a first response factor data set acquired from a gas chromatograph apparatus during a procedure on a calibration or reference gas sample at a first time;

receiving one or more additional response factor data sets acquired from the gas chromatograph apparatus during a procedure on a calibration or reference gas sample from one or more later times;

calculating a measure of uncertainty of at least one compound of the reference gas sample from the first and additional response factor data sets;

wherein the one or more later times are when the gas chromatograph apparatus is in situ or on site in a gas sample analysis facility.

Embodiments of the second aspect of the invention may include one or more features of the first aspect of the invention or its embodiments, or vice versa.

According to a third aspect of the invention, there is provided a method of maintaining gas chromatography apparatus, the method comprising performing the method of the first or second aspects of the invention;

comparing the measure of uncertainty with a predetermined threshold;

and identifying or scheduling a requirement for one or more maintenance operations on the gas chromatography apparatus.

The method of maintaining a chromatograph apparatus provides a means for identifying that the gas chromatograph is not in a healthy state, i.e. it may have a deteriorated column, degraded valves or the quality of the calibration gas is deficient. Therefore a value of the combined uncertainty above a predetermined threshold is indicative that a maintenance action is needed or desirable. A number of different maintenance actions are contemplated in this aspect of the invention, and include (without limitation): a general troubleshooting to identify which of the GC components is not in a correct functional state; a general maintenance service, in which all common maintenance actions are performed; or a detailed or more precise action, such as changing a GC valve, replacing the calibration gas, or changing the columns.

This method of this aspect of the invention may therefore identify a maintenance requirement based on current and historical GC performance data and presents an alternative to periodical maintenance. Periodical maintenance involves scheduling of maintenance actions based on regular periods of service time. However, a GC apparatus does not necessarily need a maintenance action after a predetermined period of service, which can lead to a waste of time and economical resources in unnecessary maintenance. On the other hand, the present method can also identify necessary maintenance actions which in a periodical maintenance scheme would not be addressed until the next periodically scheduled maintenance action. This is also an advantage because avoids the gas chromatograph being operated in an unhealthy state, which could result in inaccurate measurements of gas compositions and inaccurate gas transactions taxing and payments.

Embodiments of the third aspect of the invention may include one or more features of the first or second aspects of the invention or their embodiments, or vice versa.

According to a fourth aspect of the invention, there is provided a computerised method of analysing gas chromatography data comprising performing the method of the first aspect of the invention in a computer system.

Embodiments of the fourth aspect of the invention may include one or more features of any of the first to third aspects of the invention or its embodiments, or vice versa.

The methods of the various aspects of the invention and/or the critical steps thereof are preferably implemented in software, although it will be understood that the methods or steps thereof may also be implemented in firmware or hardware or in combinations of software, firmware or hardware.

BRIEF DESCRIPTION OF THE DRAWINGS

There will now be described, by way of example only, various embodiments of the invention with reference to the drawings and examples, of which.

DETAILED DESCRIPTION OF PREFERRED EMBODIMENTS

By way of example only, embodiments of the invention are described in applications of gas chromatography to the analysis of hydrocarbon-containing gas samples, for example natural gas samples. Applications to $C_{6+}$ GC systems are described, but the invention is not so limited and its principles may be applied to other GC systems. The embodiments are generally described as being implemented in a computer system and it will be appreciated that the invention may be implemented in software, hardware, firmware, or a combination thereof.

Figure 1:
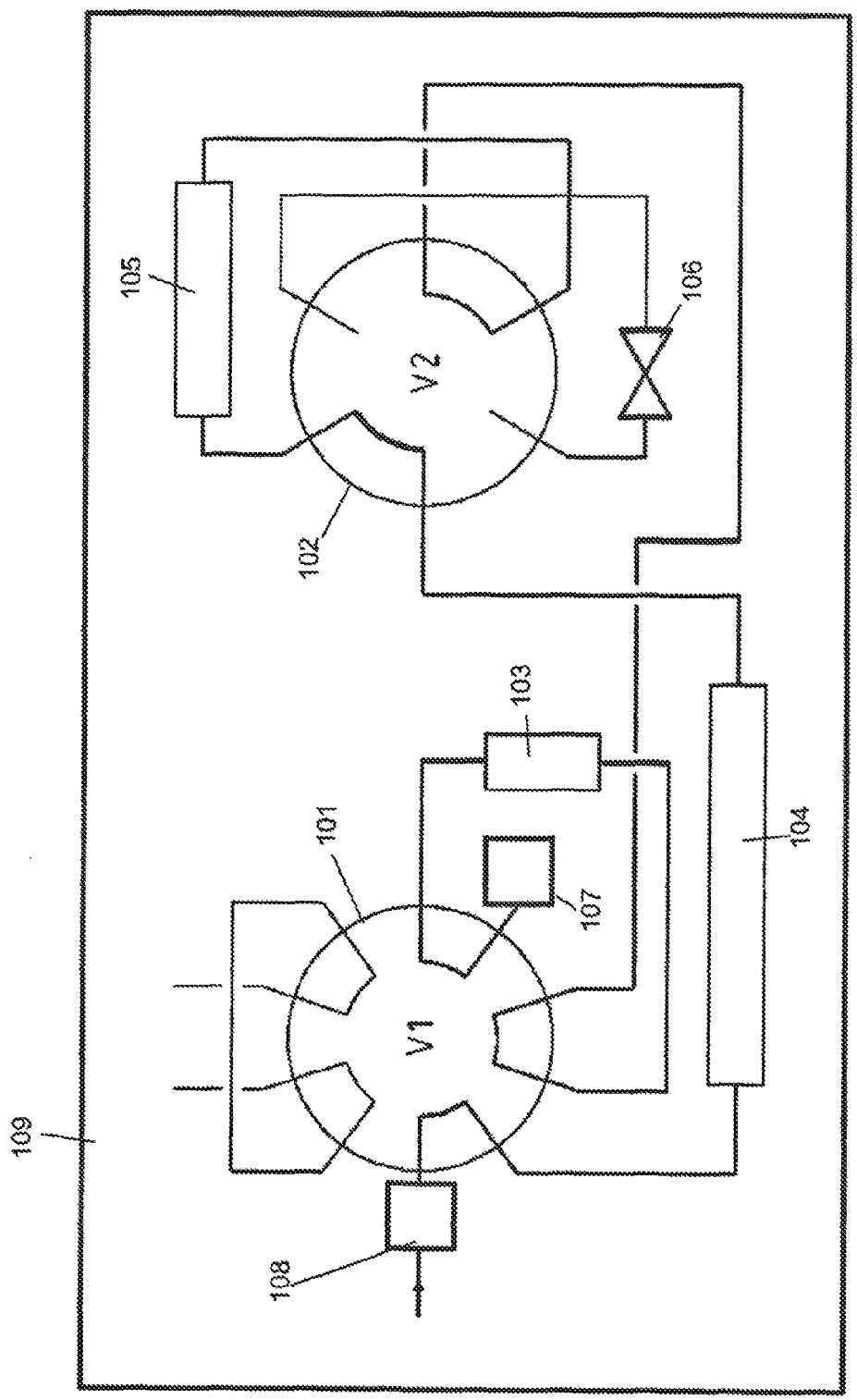
FIG. 1 shows schematically a typical three-column gas chromatograph.
Figure 2:
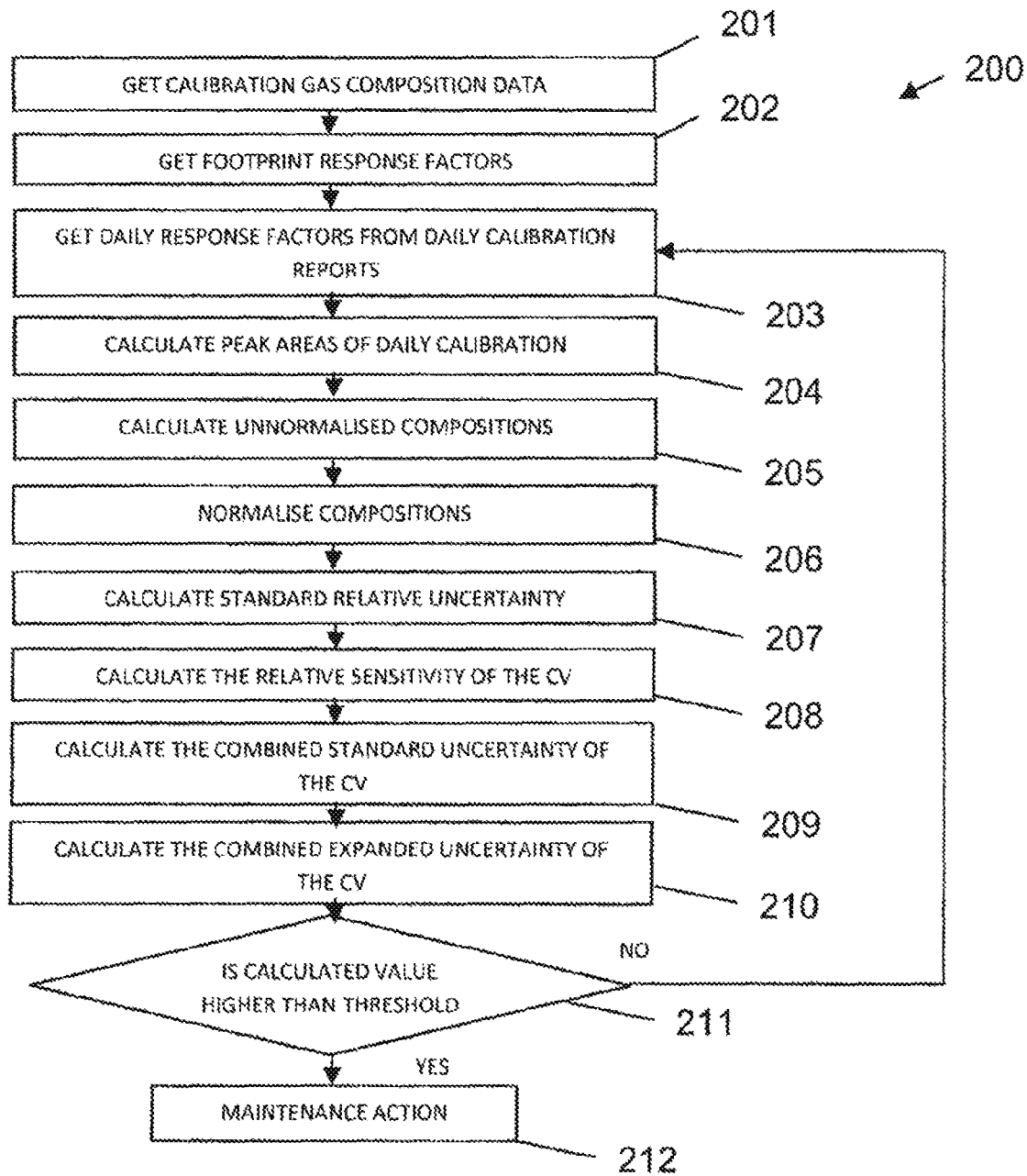
FIG. 2 is a block diagram of the method of GC Condition Based Monitoring using historical calibration data for updated combined uncertainty calculation according to a first embodiment of the invention.

Referring firstly to FIG. 2, there is shown a block diagram representing the steps of a method 200 in accordance with a first embodiment of the invention. This is a method 200 of GC Condition Based Monitoring for calculating updated or live uncertainty using historical calibration data. This method can also be described as an expert system for identifying maintenance requirements.

In this example, the GC has been calibrated in the factory using a conventional multilevel calibration technique, and a repeatability relative uncertainty value for the apparatus is calculated using standard methodology. This repeatability relative uncertainty value may then be used in the assessment of uncertainty in calorific value calculations on data acquired from tests of gas samples, as is known in the art.

With the GC apparatus in situ, the first step 201 of the method is to obtain the composition (Comp), which in the industry standard is referred to as ($x_{i,wrm}$) of a calibration gas which is to be used for the periodical calibrations. This is obtained when the GC apparatus is assumed to be in a good condition. The response factors from this initial calibration gas measurement ($RF_{i,FP}$) are determined and are used as reference or footprint data (step 202). The "footprint data" is data acquired from the gas chromatography apparatus in a known healthy condition such as after a multilevel calibration.

The third step 203 is to obtain the response factors ($RF_{i,cal}$) of one or more calibration reports, acquired throughout the operational period of the GC apparatus and after the initial calibration gas measurement. Historical response factors ($RF_{i,cal}$) obtained from regular calibrations of the GC may be used, and can be obtained from a GC maintenance software installed in a computer connected to the GC which automatically or manually receives periodical calibration data. Alternatively these data can also be obtained from a written register of periodical calibration data.

The previous data is received in a computer system, which is preferably a personal computer programmed to execute the steps of the method. The computer system can be interfaced with the GC. Alternatively the computer system can be connected via the internet to the GC operational system. The method can also be performed using data collected and stored in a GC at an earlier time The next step 204 is to calculate a peak area (PA), which in the industry standard is referred to as ($R_{i,cal}$), for every component of the calibration gas from the last calibration data using the formula:

$$PA = RF_{cal} \times \text{Calibration gas composition (\% mol)} \quad (Eq. 3)$$

which in the industry standard terminology is given by:

$$R_{i,cal} = RF_{i,cal} \times x_{i,wrm} \quad (Eq. 4)$$

where PA or $R_{i,cal}$ is peak area and $RF_{i,cal}$ is response factor from a periodical calibration.

In the next step 205, the unnormalised composition (Un-Comp, which in the industry standard is referred to as ($x_i^*$)) of the calibration gas is calculated using the calibration peak areas obtained in the previous step and the reference (or footprint) response factors, according to the formula:

$$\text{Unnormalised composition} = PA/RF_{foot} \quad (Eq. 5)$$

which in the industry standard terminology is given by;

$$x_i^* = \frac{R_{i,cal}}{RF_{i,FP}} \quad (Eq.6)$$

The present method uses normalised compositions for calculating the uncertainty of the GC measurements (or derived gas properties) from the repeatability and from the reproducibility data obtained during an operational period of the GC. It has been found that this is more effective than using unnormalised compositions for calculating the uncertainty of the GC measurements (or derived gas properties) from the repeatability data, as the present method of calculating the uncertainty of the GC measurements does not reflect an overestimation of uncertainty due to changes in the composition of the calibration gas. The use of unnormalised compositions in calculating the uncertainty could be more sensitive to changes in the calibration gas composition.

The next step 206 is to normalise the compositions obtained in the previous step. In this context, normalise means to express in % mol the composition of a gas containing the quantities of gas expressed by the unnormalised compositions figures. The normalised composition (N-Comp, which in industry standard is referred to as ($x_i$)) of a component can be expressed as:

$$N\text{-Comp (\% mol)} = (\text{Un-Comp/sum of all unnormalised compositions of the components in the calibration gas}) \times 100 \quad (Eq. 7)$$

which in industry standard terminology is given by:

$$x_i = \frac{x_i^*}{\sum_{i=1}^{q} x_i^*} \times 100 \quad \text{(Eq.8)}$$

The previous steps are preferably done on a regular basis, for example most preferably on a daily basis. These method steps may be preferably carried out after every calibration, and therefore may use all available calibration data. However, it is not necessary to use data from each calibration, and the measure of uncertainty data may be updated at regular or irregular intervals during a period of operation. For example, the steps may be carried out after a selected number of calibrations or after a selected operational period.

In order to calculate a live or updated uncertainty in the Calorific Value (CV) of the GC reproducibility measurements in the actual GC state, the following steps are followed.

Firstly, it is necessary to calculate for each component of the calibration gas the standard deviation of the composition of the calibration gas using the historical data from regular calibrations. The standard deviation is a well known statistical parameter, which may be calculated according to the following formula:

$$s(x_i) = \sqrt{\frac{\sum_{n=1}^{N}(x_{i,n} - \bar{x}_i)}{N-1}} \quad \text{(Eq.9)}$$

Here, N represents the number of historical calibrations since the last footprint data was taken; $x_i$ represents the i-th measured normalised mol fraction of a given component using the i-th measured response/peak area and the response factor from the footprint data; and $\bar{x}_i$ represents the average measured normalised mol fraction of each component when measured using the response factor from the footprint data.

In the next step 207 the reproducibility relative uncertainty $U_{rpd}(x_i)$ for a component is calculated by dividing the standard deviation of the normalised historical calibration data by the concentration of that component in the working reference mixture according to:

$$U_{rpd}(x_i) = \frac{s(x_i)}{x_{i,wrm}} \quad \text{(Eq.10)}$$

Calculation of the calorific value (CV) of a gas of known composition is performed by a conventional method. The next step 208 is to calculate the relative sensitivity of the calorific value of natural gas of standard composition for every component of the calibration gas. This is done by dividing the relative change in calorific value produced by a change in a certain component's concentration value by the relative change in the certain component's concentration.

The third step 209 is to calculate the Combined Standard Uncertainty of the Calorific Value of the natural gas by adding the squares of the products of each component's CV sensitivity by each component's relative uncertainty, and square-rooting the result. The Combined Standard Uncertainty is the sum of the previous calculations for all the components of the gas.

The next step 210 is to calculate the Combined Expanded uncertainty of the Calorific Value by multiplying the Combined Standard Uncertainty of the Calorific Value by a numerical coverage factor, which may be for example a factor of 2.

In the final step 211 the Combined Expanded Uncertainty value obtained is compared to a threshold value. If the calculated combined expanded uncertainty value is above of the threshold value, then a signal output in the form of, for example a sound, light, alarm, colour change is triggered indicating a maintenance action requirement 212.

According to this embodiment, the gas chromatography data is analysed and transformed to produce an output signal indicative of a healthy or unhealthy condition of the GC. By analysing this information, it can be determined when to intervene and perform maintenance on the GC system before it enters an unhealthy state.

The method described herein uses historical reference or footprint data generated when the GC is known or assumed to be functioning correctly. Data such as oven temperature, carrier gas pressure, carrier gas flow rate, response factor etc. are recorded. These footprint values can be used as a tool to analyze historical calibration results. This is in contrast to the prior art techniques, which take in account uncertainty only from a simplified repeatability analysis. The present method considers uncertainty derived also from reproducibility data obtained from periodical calibrations with the footprint data as reference.

The previously described example is an embodiment of the invention in which the uncertainty calculation is associated to the calculation of the Calorific Value of the gas, but this must not be taken as a limitation of the principles of the invention. It will be appreciated that other gas properties can be calculated. Other desired gas properties that could be calculated include (without limitation) density, thermal conductivity, compressibility, and molecular weight.

Figure 3:
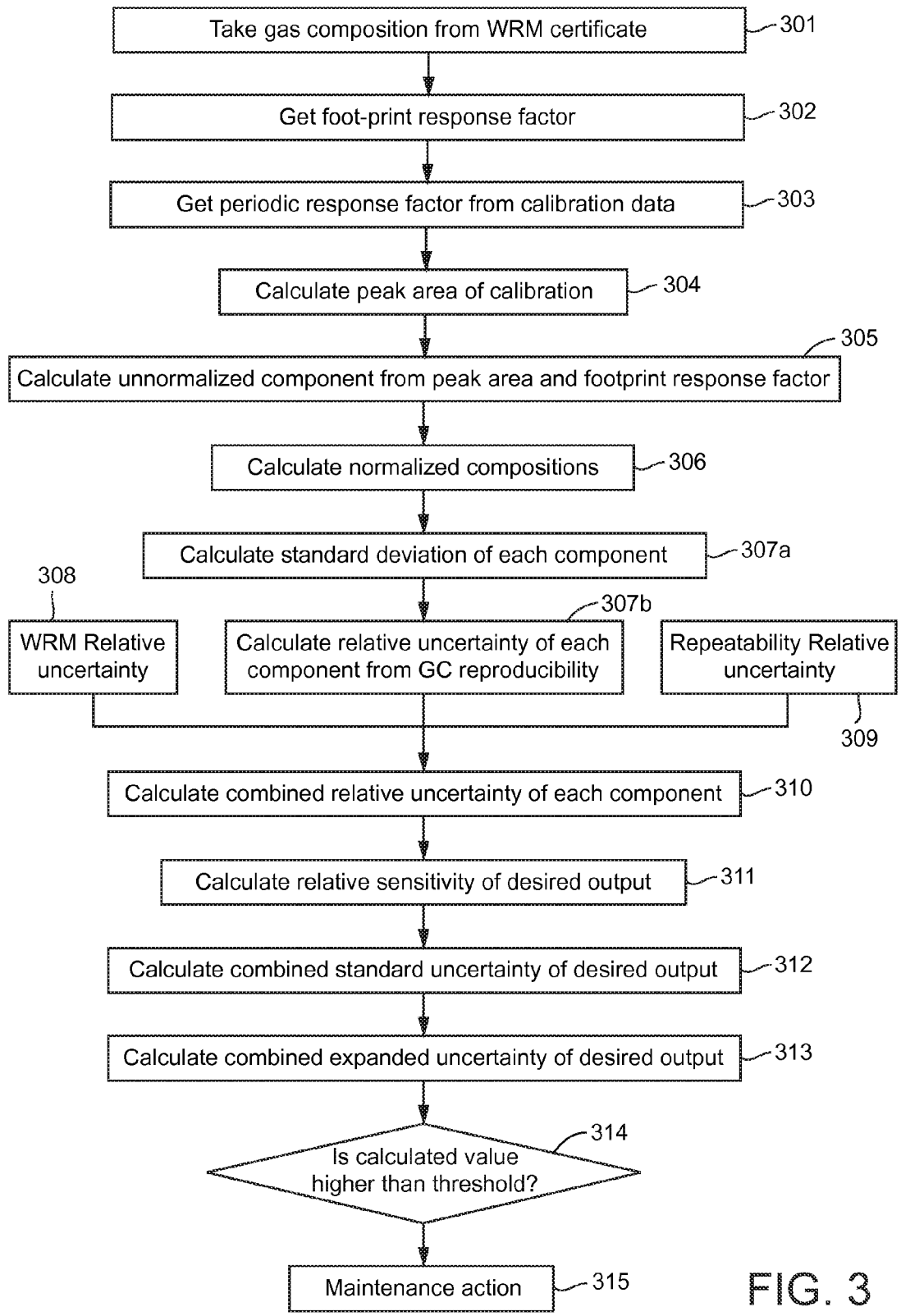
FIG. 3 is a block diagram of the method of GC Condition Based Monitoring using historical calibration data for updated combined uncertainty calculation according to a second embodiment of the invention.

FIG. 3 depicts a method, generally referred to at 300, according to an alternative embodiment of the invention in which the uncertainty calculation is not associated with the calculation of any specific gas property. The method 300 is similar to the method 200 and will be understood from FIG. 2 and the accompanying description. In the method of FIG. 3 the steps refer to any desired output of a gas property that can be calculated and is dependent on the gas composition.

The initial steps 301 to 306 of the method of FIG. 3 are equivalent to the initial steps 201 to 206 of the method of FIG. 2 and will not be described again for reasons of brevity.

In the method 300, the step of calculating a reproducibility relative uncertainty is shown as two 307a and 307b (as opposed to the single step 207 in FIG. 2). In sub-step 307a, the standard deviation of each component is calculated. In step 307b, the standard relative reproducibility uncertainty is calculated.

The method 300 of FIG. 3 comprises the additional step 310 of calculating a combined relative uncertainty of each component gas from the standard relative reproducibility uncertainty (from 307a, a calibration gas or working reference mixture relative uncertainty 308; and a repeatability relative uncertainty 309.

To obtaining the calibration gas relative uncertainty $U_{wrm}$ ($x_i$) (step 308) it is normally sufficient to check the United Kingdom Accreditation Service (UKAS) certification accompanying the gas cylinder which provides the working reference mixture relative uncertainty.

To calculating the repeatability relative uncertainty in step 309 the procedure described in ISO 10723 can be followed. The standard deviation of the response for each component is then expressed as:

$$s_i = a + b \times x_i^* + c \times x_i^2 + d \times x_i^3 \qquad \text{(Eq. 11)}$$

$s_i$ is standard deviation a, b, c, d are the coefficients of linear regression of $s_i$ on $s_i^*$ $x_i^*$ is un-normalised concentration of component i The repeatability of each measured component is a function of the repeatability of the response on the working reference mixture (calibration gas) and the repeatability of the response at the concentration being measured. The calculation of the standard deviation of the sample mixture is described in both ISO 6974-2 and ISO 10723. The following equation is defined in ISO 10723:

$$\left[\frac{s(x_i^*)}{x_i^*}\right]^2 = \left[\frac{s(y_{is})}{y_{is}}\right] + \left[\frac{s(y_{istd})}{y_{istd}}\right]^2 \qquad \text{(Eq.12)}$$

Where:

$y_{is}$ and $y_{istd}$ are the instrument responses to component i in the sample and standard $s(y_{is})$ and $s(y_{istd})$ are the respective standard deviations;

$x_i^*$ is the un-normalised concentration of component i; and $s(x_i^*)$ is the standard deviation of the un-normalised components $x_i^*$ Having calculated the standard deviation of each un-normalised component, the standard deviation of the normalised mole fractions as defined by ISO 6974-2 is given:

$$s(x_i) = x_i \times \sqrt{\frac{1 - 2x_i^*}{x_i^{*2}} \times s(x_i^*)^2 + \sum_{w=1}^{q} s(x_w^*)^2} \qquad \text{(Eq.13)}$$

Where:

$x_i$ is the normalised mole fraction of component i; and $x_i^*$ is the un-normalised mole fraction of component i The repeatability associated relative uncertainty $U_{rpt}(x_i)$ is then calculated according to the following expression:

$$U_{rpt}(x_i) = \frac{s(x_i)}{x_{i,wrm}} \qquad \text{(Eq.14)}$$

The combined relative uncertainty $U_{com}(x_i)$ is then calculated by combining the repeatability relative uncertainty $U_{rpt}(x_i)$; from the calibration gas relative uncertainty $U_{wrm}(x_i)$ and the previously calculated reproducibility relative uncertainty U, using the following expression:

$$U_{com}(x_i) = \sqrt{(U_{wrm}(x_i))^2 + (U_{rpt}(x_i))^2 + (U_{rdp}(x_i))^2} \qquad \text{(Eq. 15)}$$

The output of step 310 in FIG. 3 is equivalent to the output of step 207 of FIG. 2, and from this point until the last step, both methods are again similar and have equivalent method steps which will not be repeated for reasons of brevity (i.e. steps 311 to 315 of FIG. 3 are equivalent to steps 208 to 2012 of the method of FIG. 2).

The method 300 may provide a more balanced value of the live or updated uncertainty compared to the method 200, because it takes into account different sources of uncertainty to provide a combined uncertainty measure. Therefore the identification of a maintenance action requirement may be more consistent with the actual state of the GC.

Figure 4:
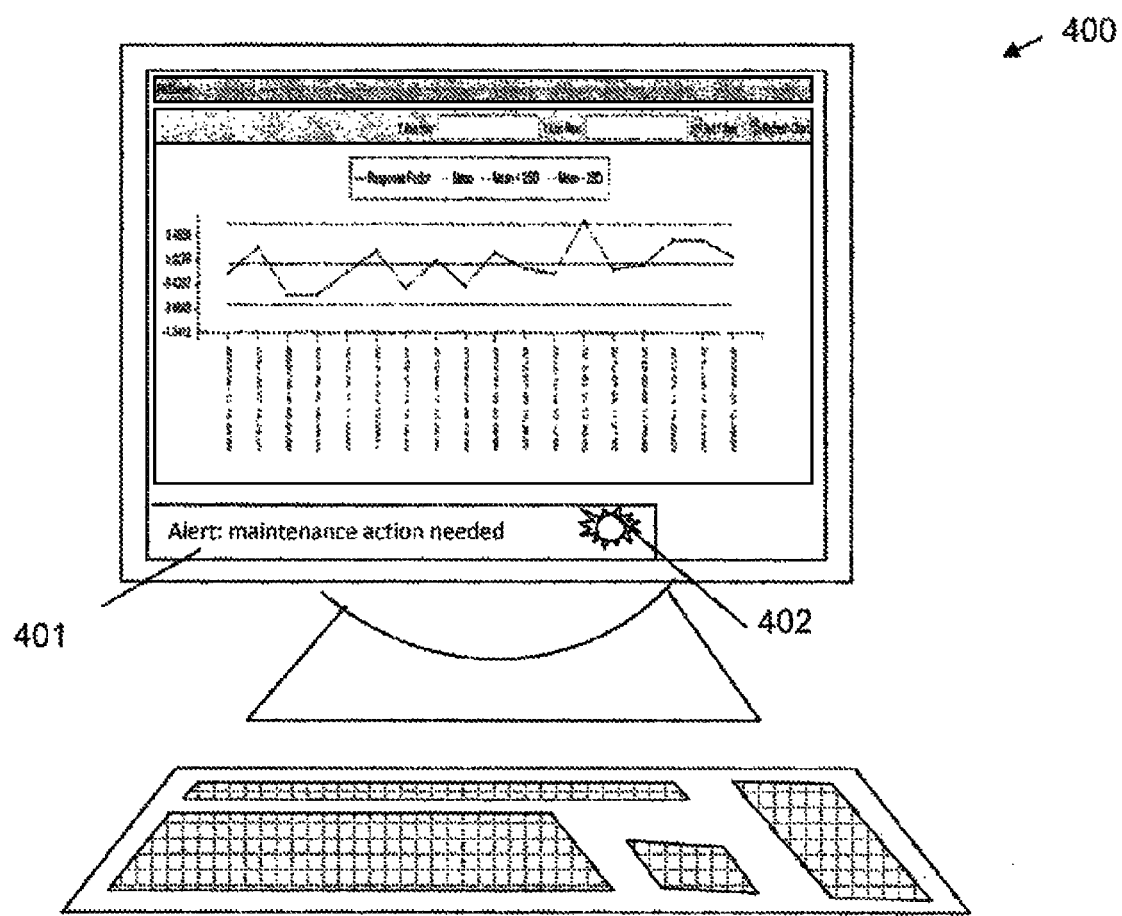
FIG. 4 is a schematic representation of a computer performing the method of GC Condition Based Monitoring using a combined uncertainty calculation.

The methods of the present invention are preferably implemented in software and executed in a computer system. FIG. 4 shows schematically a computer 400 performing the method 300 of GC Condition Based Monitoring (shown in FIG. 3) using a combined uncertainty calculation.

The computer 400 is configured to execute a software program to perform the calculations and comparisons of the method 300. According to the method, the software generates output data displays and generates a signal to the computer to display an alert message 401 that reads "maintenance action required". This informs the operator (not shown) that it is necessary to and schedule an appropriate maintenance action. There may be an audible signal 402 for making the alert message more prominent or noticeable.

This embodiment of the invention is described by way of example only and it will be understood that other variations can be implemented without departing from the principles of invention. For example the alert message could be an SMS message sent to a distant mobile phone or an e-mail sent to an e-mail account. Other types of alert messages could be used.

The invention provides a method of analysing gas chromatography data. The method uses historical calibration data collected during an operational period of the GC or when the GC is on-site to calculate an uncertainty value representative of the current condition of the GC, i.e. a "live or updated" uncertainty value. The live uncertainty value is linked to a calculated gas property, for example its calorific value, density, or compressibility. and may be compared with a threshold value in order to, for example, identify the necessity to perform a maintenance action in the GC or to assess whether the GC is in a healthy or unhealthy condition.

The present invention provides improved methods of analysing gas chromatography data, and in particular, improved methods of uncertainty monitoring for gas chromatography apparatus. The invention provides methods of calibrating, monitoring and/or maintaining gas chromatography equipment which permit monitoring a GC whilst also providing an on-line estimate of the overall uncertainty in the natural gas composition measurements. The methods are improved with respect to the prior art by providing an accurate and up to date uncertainty calculation which facilitates monitoring and maintenance scheduling methods for on-site gas chromatographs.

Various modifications may be made within the scope of the invention as herein intended, and embodiments of the invention may include combinations of features other than those expressly claimed. Although embodiments of the invention are described with reference to three-column gas chromatographs, the principles of the invention can be applied to other types of gas chromatography system.

REFERENCES

[1] S. Fosse, R. Sakariassen, and F. Teknikk, "Online gas chromatography: A technical and historical overview—design and maintenance advices to achieve an accurate end result," *North Sea Flow Measurement Workshop*, 2010.

[2] J. Witte, "Further developments in the design & implementation of an advanced online condition based monitoring system & a dirty meter prediction model for custody transfer ultrasonic gas flow meters," *North Sea Flow Measurement Workshop*, 2011.

[3] M. Rensing and T. J. Cunningham, "Coriolis flowmeter verification via embedded modal analysis," *IMAC xxvIII*, 2010.

[4] M. Skelton, S. Barrons, J. Ayre, and R. Steven, "Developments in the self-diagnostic capabilities of orifice plate meters," *North Sea Flow Measurement Workshop,* 2010.

[5] A. Sutan, C. Johnson, and J. Laidlaw, "Three columns gas chromatograph analysis using correlation between component's molecular weight and its response factor," *North Sea Flow Measurement Workshop,* 2009.

[6] D. Pettigrw, "Advances in on-line gas chromatography in the natural gas industry," *North Sea Flow Measurement Workshop,* 2000.

[7] C. Cowper and R. Mounce, "Evaluation of on-line chromatograph performance," *North Sea Flow Measurement Workshop,* 1997.

[8] M. Crane, R. Beaty, and W. Lake, "Calibration of gas chromatograph for improved performance," *North Sea Flow Measurement Workshop,* 1995.

[9] ISO 10723 Natural gas: performance evaluation for on-line analytical systems. International Organization for Standardization

[10] ASTM D1945 Standard test method for analysis of natural gas by gas chromatography. American Society for testing and Materials.

[11] ISO 6974 Determination of composition with defined uncertainty by gas chromatography. International Organization for Standardization.

The invention claimed is:

1. A method of monitoring a gas chromatograph apparatus comprising:
   receiving a first response factor data set acquired from a gas chromatograph (GC) apparatus during a procedure on a calibration or reference gas sample at a first time;
   receiving one or more additional response factor data sets acquired from the gas chromatograph apparatus during a procedure on a calibration or reference gas sample from one or more later times, wherein the one or more later times are during an operational period of the gas chromatograph apparatus;
   calculating a measure of uncertainty for at least one compound of the reference gas sample from the first and additional response factor data sets, wherein calculating a measure of uncertainty comprises calculating a relative sensitivity of a desired gas property to a change in concentration of at least one compound;
   comparing the calculated measure of uncertainty to a predetermined threshold value to determine an operating condition of the GC apparatus;
   identifying or scheduling a requirement for one or more maintenance operations on the GC apparatus based on a result of the comparison of the calculated measure of uncertainty to the predetermined threshold value; and
   performing at least one of the identified or scheduled maintenance operations.

2. The method according to claim 1, wherein the one or more additional response factor data sets comprises a plurality of data sets acquired over the operational period.

3. The method according to claim 2, wherein the one or more additional response factor data sets comprises data sets acquired at regular or irregular intervals interspersed between performing tests on unknown gas samples, and wherein the method comprises calculating an updated measure of uncertainty data at regular or irregular intervals during the period of operation.

4. The method according to claim 2, comprising calculating the measure of uncertainty data after every calibration of the GC.

5. The method according to claim 1, wherein calculating a measure of uncertainty comprises calculating a combined relative uncertainty value.

6. The method according to claim 5, comprising calculating the combined relative uncertainty value by combining two or more of: a relative uncertainty of the calibration gas, an uncertainty of at least one compound derived from the GC reproducibility and/or a repeatability relative uncertainty.

7. The method according to claim 5, comprising calculating a combined relative uncertainty value for multiple compounds.

8. The method according to claim 1, wherein the calibration or reference gas sample is a working reference mixture.

9. The method according to claim 1, wherein the operational period is a period in which the gas chromatograph apparatus is in normal use.

10. The method according to claim 1, comprising calculating the measure of uncertainty data using historical reference data generated when the GC is known or assumed to be functioning correctly.

11. The method according to claim 1, wherein calculating a measure of uncertainty comprises calculating normalised compositions derived from calculated peak areas and/or historical response factors.

12. The method according to claim 1, wherein calculating a measure of uncertainty comprises calculating a standard relative uncertainty.

13. The method according to claim 1, wherein calculating a measure of uncertainty comprises calculating a combined standard uncertainty of a gas property by combining a calculated relative sensitivity of a desired gas property with a standard relative uncertainty.

14. The method according to claim 1 wherein calculating a measure of uncertainty comprises calculating a combined relative uncertainty value, and wherein calculating a combined standard uncertainty of a gas property comprises combining a calculated relative sensitivity of the desired gas property with a combined relative uncertainty.

15. The method according to claim 1, wherein calculating a measure of uncertainty comprises calculating a combined expanded uncertainty of a gas property.

16. The method according to claim 1, wherein the maintenance operation is selected form the group comprising: a valve replacement, a column replacement, a calibration gas replacement, a troubleshooting method; or a general maintenance.

17. A computerised method of analysing gas chromatography data comprising performing the method of claim 1 in a computer system.

18. A method of analysing gas chromatography data using a gas chromatograph comprising:
   receiving a first response factor data set acquired from a gas chromatograph apparatus during a procedure on a calibration or reference gas sample at a first time;
   receiving one or more additional response factor data sets acquired from the gas chromatograph apparatus during a procedure on a calibration or reference gas sample from one or more later times, wherein the one or more later times are when the gas chromatograph apparatus is in situ or on site in a gas sample analysis facility; and
   calculating a measure of uncertainty for at least one compound of the reference gas sample from the first and additional response factor data sets, wherein calculating a measure of uncertainty comprises calculating a relative sensitivity of a desired gas property to a change in concentration of at least one compound;

comparing the calculated measure of uncertainty to a predetermined threshold value to determine an operating condition of the GC apparatus;

identifying or scheduling a requirement for one or more maintenance operations on the GC apparatus based on a result of the comparison of the calculated measure of uncertainty to the predetermined threshold value; and performing at least one of the identified or scheduled maintenance operations.

19. The method according to claim 1, wherein the one or more maintenance operations is selected form the group consisting of: a general troubleshooting to identify components of the GC which are not in a correct functional state; a general maintenance service in which at least one common maintenance action is performed; changing a GC valve; replacing the calibration gas; or changing one or more columns.

* * * * *